(12) United States Patent
Rosenberg

(10) Patent No.: US 6,638,765 B1
(45) Date of Patent: Oct. 28, 2003

(54) PLATFORM FOR THE DIFFERENTIATION OF CELLS

(75) Inventor: Lawrence Rosenberg, Cote St-Luc (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/890,717

(22) PCT Filed: Feb. 2, 2000

(86) PCT No.: PCT/CA00/00105

§ 371 (c)(1),
(2), (4) Date: Aug. 3, 2001

(87) PCT Pub. No.: WO00/46351

PCT Pub. Date: Aug. 10, 2000

Related U.S. Application Data

(60) Provisional application No. 60/118,790, filed on Feb. 4, 1999.

(51) Int. Cl.[7] ............... C12N 5/00; C12N 5/02; C12N 5/08; A01N 63/00; A01N 65/00; A61K 35/39

(52) U.S. Cl. ............ 435/377; 435/325; 435/366; 435/375; 435/377; 435/395; 424/93.7; 424/562

(58) Field of Search ............. 435/366, 1.3, 380; 424/93.1

(56) References Cited

U.S. PATENT DOCUMENTS 5,681,587 A * 10/1997 Halberstadt et al. ........ 424/562

FOREIGN PATENT DOCUMENTS

| WO | WO95/29989 | 11/1995 |
| WO | WO97/15310 | 5/1997 |
| WO | WO97/16536 | 5/1997 |
| WO | WO00/46351 A3 | 8/2000 |

OTHER PUBLICATIONS

L Rosenberg, Cell Transplantation, "In Vivo Cell Transformation:Neogenesis of Beta Cells from Pancreatic Ductal Cells," 1995, vol. 4, No. 4, pp. 371–383.*
Yuan, Songyang et al., "Transdifferentiation of human islets . . . ", Differentiation, (1996) 61, pp. 67–75.
Hulinsky, Ilja et al., "Insulin secretion and DNA synthesis . . . ", Pancreas, (1995) vol. 11, No. 3, pp. 309–314.
Kerr–Conte, Julie et al., "Ductal cyst formation . . . ", Diabetes, vol. 45, Aug. 1996, pp. 1108–1114.
Paraskevas, S. et al., "Apoptosis occurs in freshly . . . ", Transplantation Proceedings, (1997) 29, pp. 750–752.
Rosenburg, Lawrence, "In vivo cell transformation . . . ", Cell Transplantation, (1995) vol. 4, No. 4, pp. 371–383.

* cited by examiner

Primary Examiner—Jeffrey Fredman
Assistant Examiner—Jon Eric Angell
(74) Attorney, Agent, or Firm—Birch, Stewart, Kolasch & Birch, LLP

(57) ABSTRACT

The present invention relates to an in vitro method for islet cell expansion, which comprises the steps of: a) preparing dedifferentiated cells derived from cells in or associated with post-natal islets of Langerhans; b) expanding the dedifferentiated cells; and c) inducing islet cell differentiation the expanded cells of step b) to become insulin-producing cells.

4 Claims, 7 Drawing Sheets

(6 of 7 Drawing Sheet(s) Filed in Color)

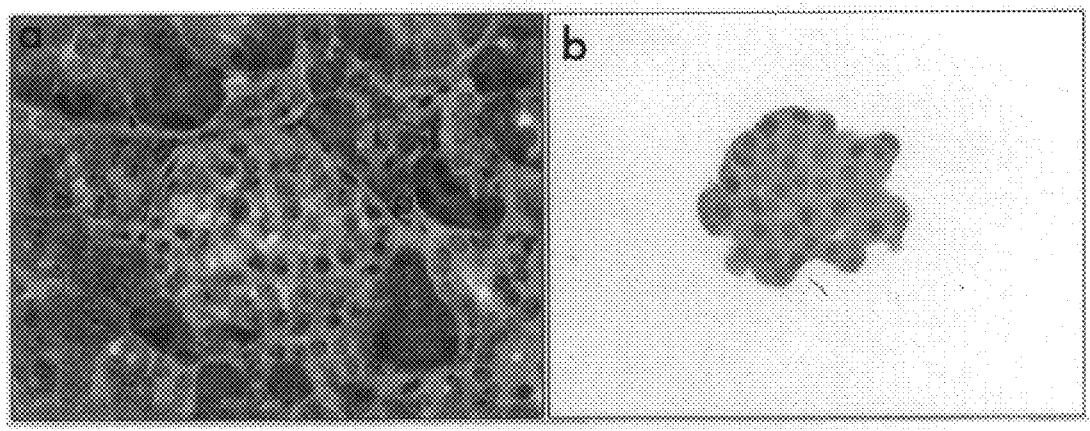
FIG._1A  FIG._1B
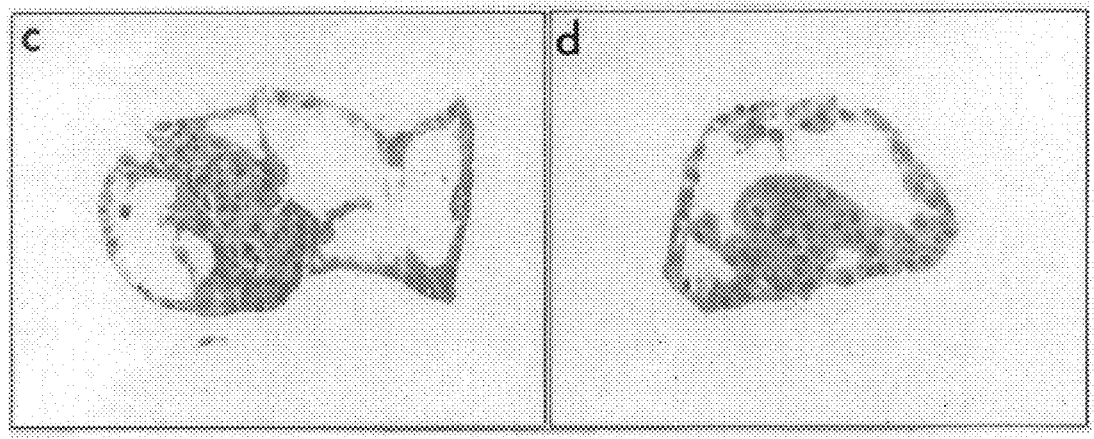
FIG._1C  FIG._1D
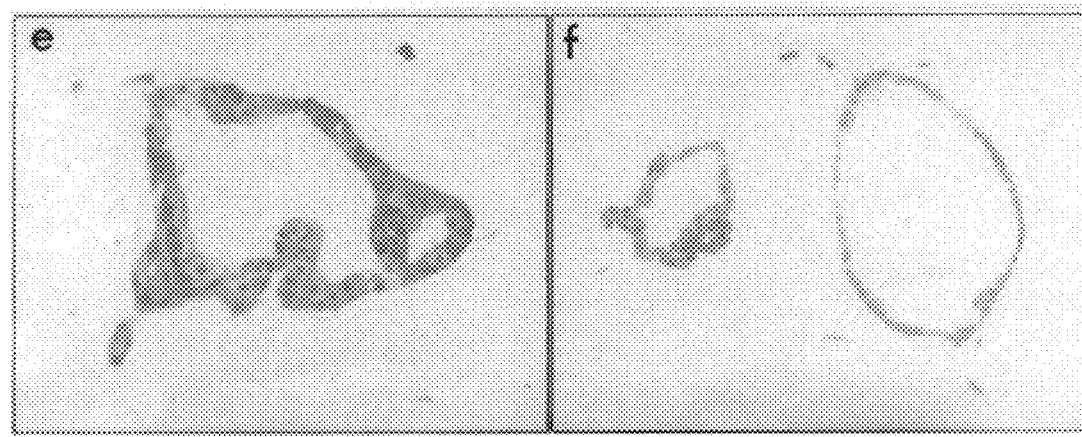
FIG._1E  FIG._1F

 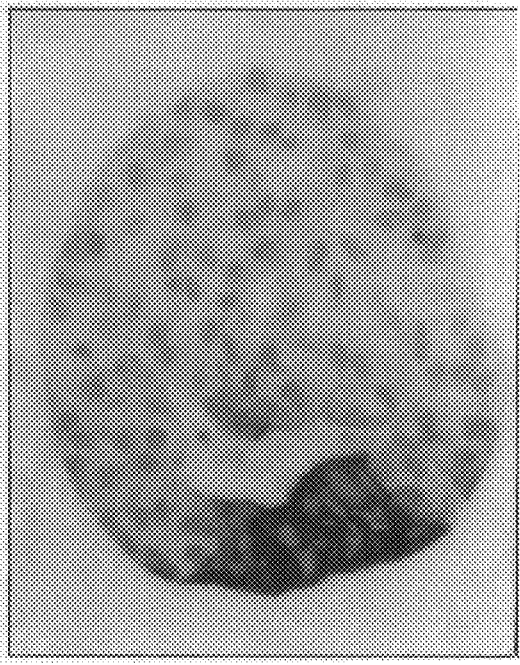
FIG. 4A   FIG. 4B
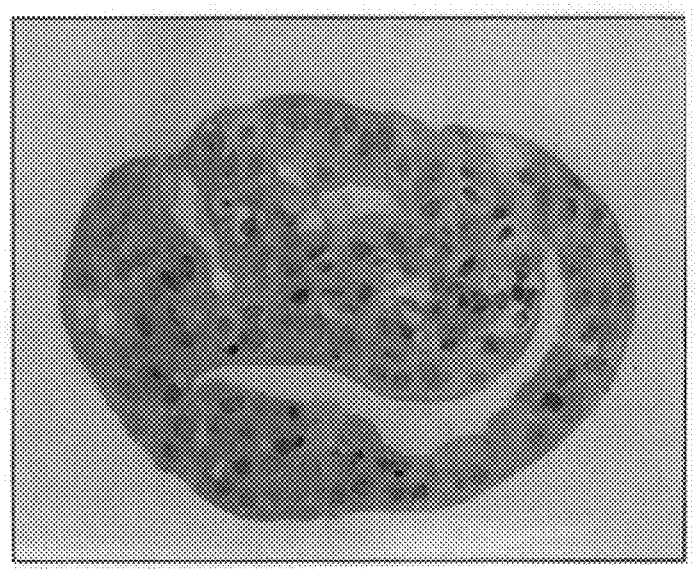
FIG. 4C

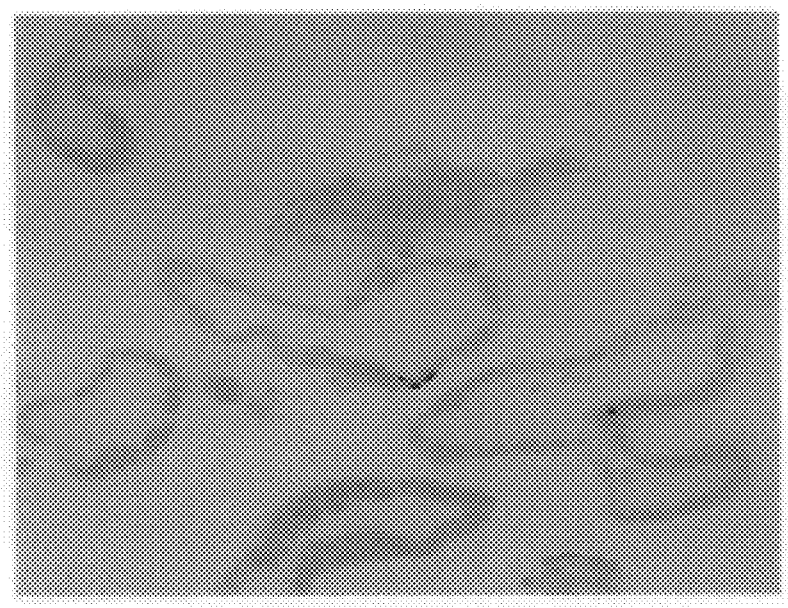
FIG_6A
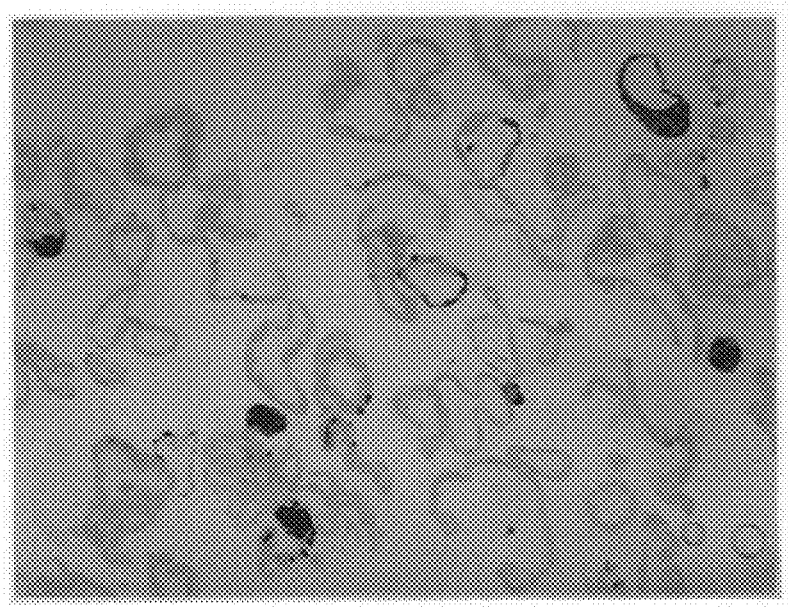
FIG_6B

PLATFORM FOR THE DIFFERENTIATION OF CELLS

This application claims the benefit of provisional application No. 60/118,790, filed Feb. 4, 1999.

BACKGROUND OF THE INVENTION (a) Field of the Invention

The invention relates to an in vitro method for islet cell expansion; an in vitro method for producing multi bipolar cells; an in vitro method for stem cell expansion; and a method for the treatment of diabetes mellitus in a patient.

(b) Description of Prior Art

Diabetes Mellitus

Diabetes mellitus has been classified as type I, or insulin-dependent diabetes mellitus (IDDM) and type II, or non-insulin-dependent diabetes mellitus (NIDDM). NIDDM patients have been subdivided further into (a) nonobese (possibly IDDM in evolution), (b) obese, and (c) maturity onset (in young patients). Among the population with diabetes mellitus, about 20% suffer from IDDM. Diabetes develops either when a diminished insulin output occurs or when a diminished sensitivity to insulin cannot be compensated for by an augmented capacity for insulin secretion. In patients with IDDM, a decrease in insulin secretion is the principal factor in the pathogenesis, whereas in patients with NIDDM, a decrease in insulin sensitivity is the primary factor. The mainstay of diabetes treatment, especially for type I disease, has been the administration of exogenous insulin.

Rationale for More Physiologic Therapies

Tight glucose control appears to be the key to the prevention of the secondary complications of diabetes. The results of the Diabetes Complications and Control Trial (DCCT), a multicenter randomized trial of 1441 patients with insulin dependent diabetes, indicated that the onset and progression of diabetic retinopathy, nephropathy, and neuropathy could be slowed by intensive insulin therapy (The Diabetes Control and Complication Trial Research Group, *N. Engl. J. Med.*, 1993; 29:977–986). Strict glucose control, however, was associated with a three-fold increase in incidence of severe hypoglycemia, including episodes of seizure and coma. As well, although glycosylated hemoglobin levels decreased in the treatment group, only 5% maintained an average level below 6.05% despite the enormous amount of effort and resources allocated to the support of patients on the intensive regime (The Diabetes Control and Complication Trial Research Group, *N. Engl. J. Med.*, 1993; 29:977–986). The results of the DCCT clearly indicated that intensive control of glucose can significantly reduce (but not completely protect against) the long-term microvascular complications of diabetes mellitus.

Other Therapeutic Options

The delivery of insulin in a physiologic manner has been an elusive goal since insulin was first purified by Banting, Best, McLeod and Collip. Even in a patient with tight glucose control, however, exogenous insulin has not been able to achieve the glucose metabolism of an endogenous insulin source that responds to moment-to-moment changes in glucose concentration and therefore protects against the development of microvascular complications over the long term.

A major goal of diabetes research, therefore, has been the development of new forms of treatment that endeavor to reproduce more closely the normal physiologic state. One such approach, a closed-loop insulin pump coupled to a glucose sensor, mimicking β-cell function in which the secretion of insulin is closely regulated, has not yet been successful. Only total endocrine replacement therapy in the form of a transplant has proven effective in the treatment of diabetes mellitus. Although transplants of insulin-producing tissue are a logical advance over subcutaneous insulin injections, it is still far from clear whether the risks of the intervention and of the associated long-term immunosuppressive treatment are lower those in diabetic patients under conventional treatment.

Despite the early evidence of the potential benefits of vascularized pancreas transplantation, it remains a complex surgical intervention, requiring the long-term administration of chronic immunosuppression with its attendant side effects. Moreover, almost 50% of successfully transplanted patients exhibit impaired tolerance curves (Wright F H et al., *Arch. Surg.*, 1989;124:796–799; Landgraft R et al., *Diabetologia* 1991; 34 (suppl 1):S61; Morel P et al., *Transplantation* 1991; 51:990–1000), raising questions about their protection against the long-term complications of chronic hyperglycemia.

The major complications of whole pancreas transplantation, as well as the requirement for long term immunosuppression, has limited its wider application and provided impetus for the development of islet transplantation. Theoretically, the transplantation of islets alone, while enabling tight glycemic control, has several potential advantages over whole pancreas transplantation. These include the following: (i) minimal surgical morbidity, with the infusion of islets directly into the liver via the portal vein; (ii) the possibility of simple re-transplantation for graft failures; (iii) the exclusion of complications associated with the exocrine pancreas; (iv) the possibility that islets are less immunogenic, eliminating the need for immunosuppression and enabling early transplantation into non-uremic diabetics; (v) the possibility of modifying islets in vitro prior to transplantation to reduce their immunogenicity; (vi) the ability to encapsulate islets in artificial membranes to isolate them from the host immune system; and (vii) the related possibility of using xenotransplantation of islets immunoisolated as part of a biohybrid system. Moreover, they permit the banking of the endocrine cryopreserved tissue and a careful and standardized quality control program before the implantation.

The Problem of Islet Transplantation

Adequate numbers of isogenetic islets transplanted into a reliable implantation site can only reverse the metabolic abnormalities in diabetic recipients in the short term. In those that were normoglycemic post-transplant, hyperglycemia recurred within 3–12 mo. (Orloff M, et. al., *Transplantation* 1988; 45:307). The return of the diabetic state that occurs with time has been attributed either to the ectopic location of the islets, to a disruption of the enteroinsular axis, or to the transplantation of an inadequate islet cell mass (Bretzel R G, et al. In: Bretzel R G, (ed) Diabetes mellitus. (Berlin: Springer, 1990) p.229).

Studies of the long term natural history of the islet transplant, that examine parameters other than graft function, are few in number. Only one report was found in which an attempt was specifically made to study graft morphology (Alejandro R, et. al., *J Clin Invest* 1986; 78: 1339). In that study, purified islets were transplanted into the canine liver via the portal vein. During prolonged follow-up, delayed failures of graft function occurred. Unfortunately, the graft was only examined at the end of the study, and not over time as function declined. Delayed graft failures have also been confirmed by other investigators for dogs (Warnock G L et. al., *Can. J. Surg.,* 1988; 31: 421 and primates (Sutton R, et. al., *Transplant Proc.,* 1987; 19: 3525). Most failures are presumed to be the result of rejection despite appropriate immunosuppression.

Because of these failures, there is currently much enthusiasm for the immunoisolation of islets, which could eliminate the need for immunosuppression. The reasons are compelling. Immunosuppression is harmful to the recipient, and may impair islet function and possibly cell survival (Metrakos P, et al., *J. Surg. Res.,* 1993; 54: 375). Unfortunately, micro-encapsulated islets injected into the peritoneal cavity of the dog fail within 6 months (Soon-Shiong P, et. al., *Transplantation* 1992; 54: 769), and islets placed into a vascularized biohybrid pancreas also fail, but at about one year. In each instance, however, histological evaluation of the graft has indicated a substantial loss of islet mass in these devices (Lanza R P, et. al., *Diabetes* 1992; 41: 1503). No reasons have been advanced for these changes. Therefore maintenance of an effective islet cell mass post-transplantation remains a significant problem.

In addition to this unresolved issue, is the ongoing problem of the lack of source tissue for transplantation. The number of human donors is insufficient to keep up with the potential number of recipients. Moreover, given the current state of the art of islet isolation, the number of islets that can be isolated from one pancreas is far from the number required to effectively reverse hyperglycemia in a human recipient.

In response, three competing technologies have been proposed and are under development. First, islet cryopreservation and islet banking. The techniques involved, though, are expensive and cumbersome, and do not easily lend themselves to widespread adoption. In addition, islet cell mass is also lost during the freeze-thaw cycle. Therefore this is a poor long-term solution to the problem of insufficient islet cell mass. Second, is the development of islet xenotransplantation. This idea has been coupled to islet encapsulation technology to produce a biohybrid implant that does not, at least in theory, require immunosuppression. There remain many problems to solve with this approach, not least of which, is that the problem of the maintenance of islet cell mass in the post-transplant still remains. Third, is the resort to human fetal tissue, which should have a great capacity to be expanded ex vivo and then transplanted. However, in addition to the problems of limited tissue availability, immunogenicity, there are complex ethical issues surrounding the use of such a tissue source that will not soon be resolved. However, there is an alternative that offers similar possibilities for near unlimited cell mass expansion.

An entirely novel approach, proposed by Rosenberg in 1995 (Rosenberg L et al., *Cell Transplantation,* 1995;4:371–384), was the development of technology to control and modulate islet cell neogenesis and new islet formation, both in vitro and in vivo. The concept assumed that (a) the induction of islet cell differentiation was in fact controllable; (b) implied the persistence of a stem cell-like cell in the adult pancreas; and (c) that the signal(s) that would drive the whole process could be identified and manipulated.

In a series of in vivo studies, Rosenberg and co-workers established that these concepts were valid in principle, in the in vivo setting (Rosenberg L et al., *Diabetes,* 1988;37:334–341; Rosenberg L et al., *Diabetologia,* 1996;39:256–262), and that diabetes could be reversed.

The well known teachings of in vitro islet cell expansion from a non-fetal tissue source comes from Peck and co-workers (Corneliu J G et al., *Horm. Metab. Res.,* 1997;29:271–277), who describe isolation of a pluripotent stem cell from the adult mouse pancreas that can be directed toward an insulin producing cell. These findings have not been widely accepted. First, the result has not proven to be reproducible. Second, the so-called pluripotential cells have never been adequately characterized with respect to phenotype. And third, the cells have certainly not been shown to be pluripotent.

More recently two other competing technologies have been proposed the use of engineered pancreatic $\beta$-cell lines (Efrat S, *Advanced Drug Delivery Reviews,* 1998;33:45–52), and the use of pluripotent embryonal stem cells (Shamblott M J et al., *Proc. Natl. Acad. Sci. USA,* 1998;95:13726–13731). The former option, while attractive, is associated with significant problems. Not only must the engineered cell be able to produce insulin, but it must respond in a physiologic manner to the prevailing level of glucose—and the glucose sensing mechanism is far from being understood well enough to engineer it into a cell. Many proposed cell lines are also transformed lines, and therefore have a neoplastic potential. With respect to the latter option, having an embryonal stem cell in hand is appealing because of the theoretical possibility of being able to induce differentiation in any direction, including toward the pancreatic $\beta$-cell. However, the signals necessary to achieve this milestone remain unknown.

It would be highly desirable to be provided with a platform for the preparation of dedifferentiated cells derived from post-natal islets of Langerhans, their expansion and the guided induction of islet cell differentiation, leading to insulin-producing cells that can be used for the treatment of diabetes mellitus.

SUMMARY OF THE INVENTION

One aim of the invention is to provide a platform for the preparation of dedifferentiated cells derived from cells in or associated with post-natal islets of Langerhans, their expansion and the guided induction of islet cell differentiation, leading to insulin-producing cells that can be used for the treatment of diabetes mellitus.

In accordance with one embodiment of the present invention there is provided an in vitro method for islet cell expansion, which comprises the steps of:

a) preparing dedifferentiated cells derived from cells in or associated with post-natal islets of Langerhans;

b) expanding the dedifferentiated cells; and c) inducing islet cell differentiation of the expanded cells of step b) to become insulin-producing cells.

Preferably, step a) and step b) are concurrently effected using a solid matrix, basal feeding medium and appropriate growth factors to permit the development, maintenance and expansion of a dedifferentiated cell population with at least bipotentiality or being multipotent.

Preferably, step c) is effected by removing cells from the matrix and resuspended in a basal liquid medium containing soluble matrix proteins and growth factors.

Preferably, the basal liquid medium is CMRL 1066 supplemented with 10% fetal calf serum, wherein the soluble matrix proteins and growth factors are selected from the group consisting of fibronectin, IGF -1, IGF-2, insulin, and NGF. The basal liquid medium may further comprise glucose concentration of at least 11 mM. The basal liquid medium may further comprise inhibitors of known intracellular signaling pathways of apoptosis and/or specific inhibitor of p38.

In accordance with another embodiment of the present invention there is provided an in vitro method for producing cells with at least bipotentiality, which comprises the steps of:

a) preparing dedifferentiated cells derived from cells in or associated with post-natal islets of Langerhans from a patient; whereby when the dedifferentiated cells are introduced in situ in the patient, the cells are expanded and undergo islet cell differentiation to become in situ insulin-producing cells.

In accordance with another embodiment of the present invention there is provided a method for the treatment of diabetes mellitus in a patient, which comprises the steps of a) preparing dedifferentiated cells derived from cells in or associated with post-natal islets of Langerhans of the patient; and b) introducing the dedifferentiated cells in situ in the patient, wherein the cells expand in situ and undergo islet cell differentiation in situ to become insulin-producing cells.

In accordance with another embodiment of the present invention there is provided a method for the treatment of diabetes mellitus in a patient, which comprises the steps of a) preparing dedifferentiated cells derived from cells in or associated with post-natal islets of Langerhans of the patient;

b) expanding in vitro the dedifferentiated cells;

c) inducing in vitro islet cell differentiation of the expanded cells of step b) to become insulin-producing cells; and d) introducing the cells of step c) in situ in the patient, wherein the cells produce insulin in situ.

For the purpose of the present invention the following terms are defined below.

The expression "post-natal islets of Langerhans" is intended to mean islet cells and associated cells, such as duct cells, of any origin, such as human, porcine and canine, among others.

The expression "dedifferentiated cells" is intended to mean cells of any origin which are stem-like cells.

BRIEF DESCRIPTION OF THE DRAWINGS

The patent or application file contains at least one drawing executed in color. Copies of this patent or application publication with color drawing(s) will be provided by the Office upon request and payment of the necessary fee.

FIG. 1 illustrates cell-type conversion from Islet to duct-like structure (human tissues), (a) let in the pancreas, (b) Islet following isolation and purification, (c) islet in solid matrix beginning to undergo cystic change, (d–f) progressive formation of cystic structure with complete loss of islet morphology.

FIG. 4 illustrates demonstration of cell phenotype by CK-19 immunocytochemistry. Upper left panel—cystic structure in solid matrix. All cells stain for CK-19, a marker expressed in ductal epithelial cells in the pancreas. Lower panel—following removal from the solid matrix, and return to suspension culture. A structure exhibiting both epithelial-like and solid components. Upper right panel—only the epithelial-like component retains CK-10 immunoreactivity. The solid component has lost its CK -19 expression, and appears islet-like.

FIG. 6 illustrates in situ hybridization for pro-insulin mRNA. Upper panel—cystic structures with virtually no cells containing the message. Lower panel—cystic structures have been removed from the matrix and placed in suspension culture. Note the appearance now, of both solid and cystic structures. The solid structures have an abundant expression of pro-insulin mRNA.

DETAILED DESCRIPTION OF THE INVENTION

Figures 2A, 2B:
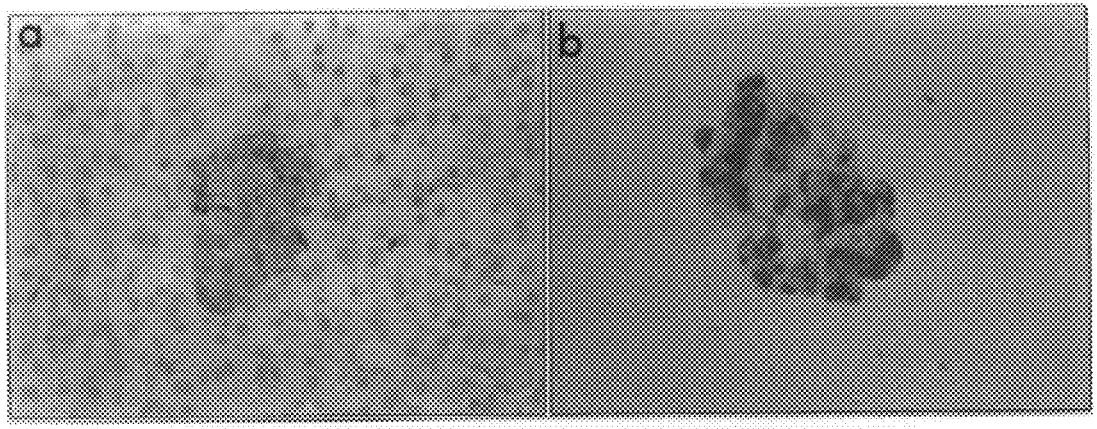
FIG. 2 illustrates same progression of changes as in FIG. 1. Cells are stained by immunocytochemistry for insulin. (a) Islet in pancreas. (b) Islet after isolation and purification. (c) Islet in solid matrix beginning to undergo cystic change. (d–e) Progressive loss of islet phenotype. (f) High power view of cyst wall composed duct-like epithelial cells. One cell still contains insulin (arrow).
Figures 2C, 2D:
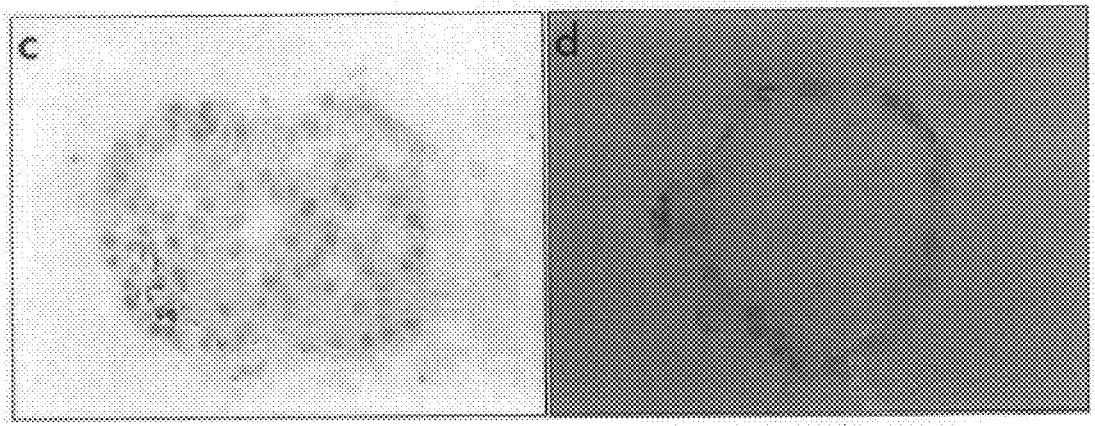
Figures 2E, 2F:
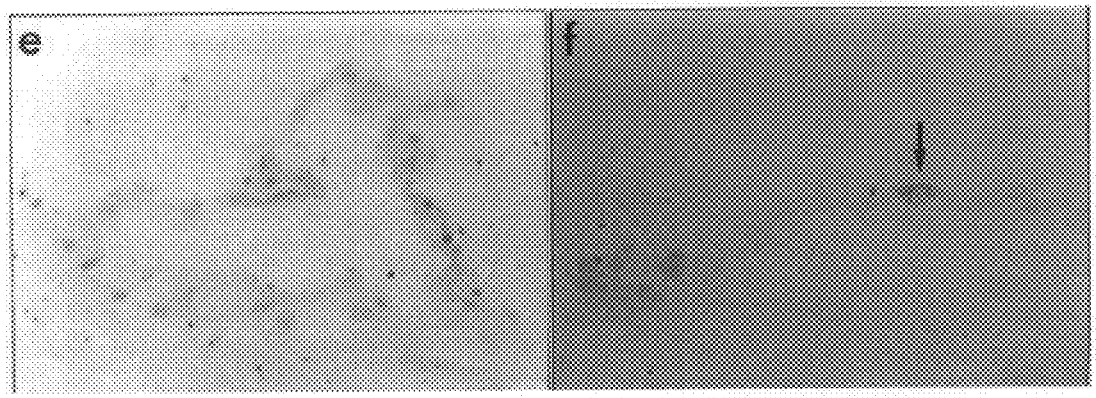
Figure 3A:
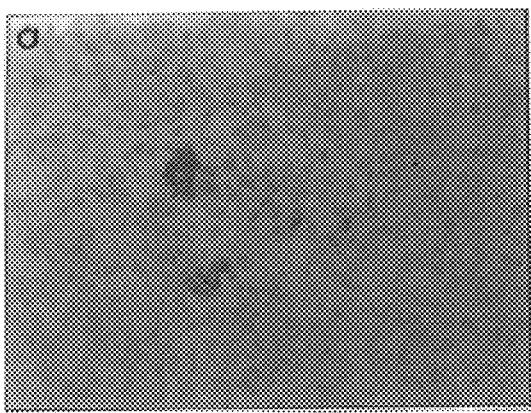
FIG. 3 illustrates same progression of changes as in FIG. 1. Cells stained by immunocytochemistry for glucagon. (a) Islet in pancreas. (b) Islet after isolation and purification. (c) Islet in solid matrix beginning to undergo cystic change. (d–e) Progressive loss of islet phenotype. (f) High power view of cyst wall composed duct-like epithelial cells. One cell still contains glucagon (arrow).
Figure 3B:
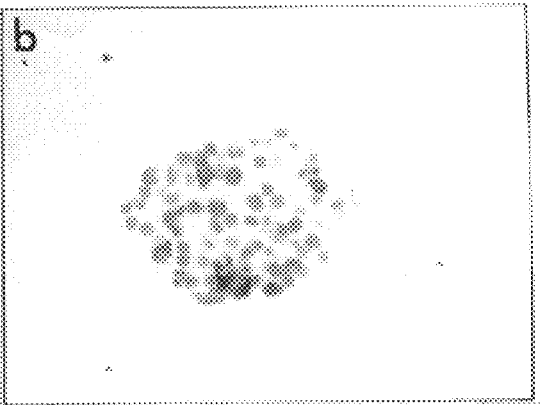
Figure 3C:
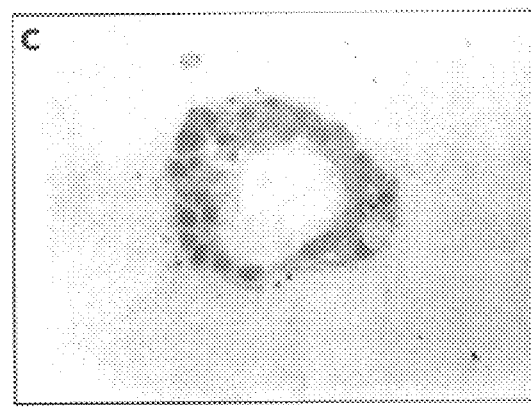
Figure 3D:
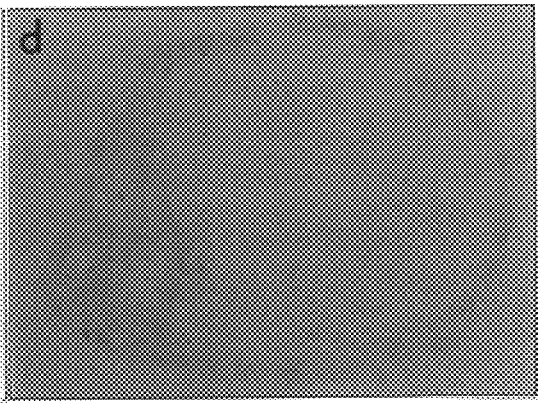
Figure 3E:
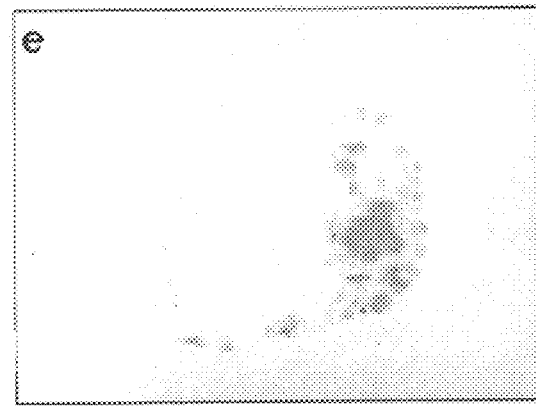
Figure 3F:
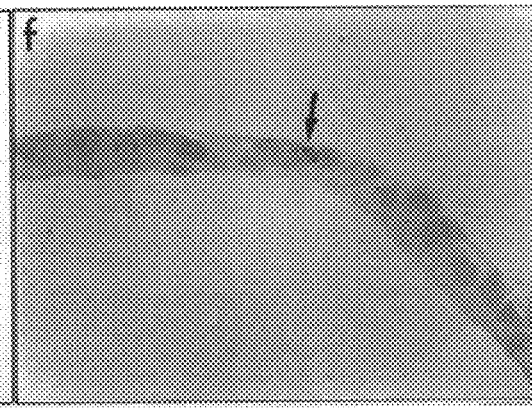
Figure 5A:
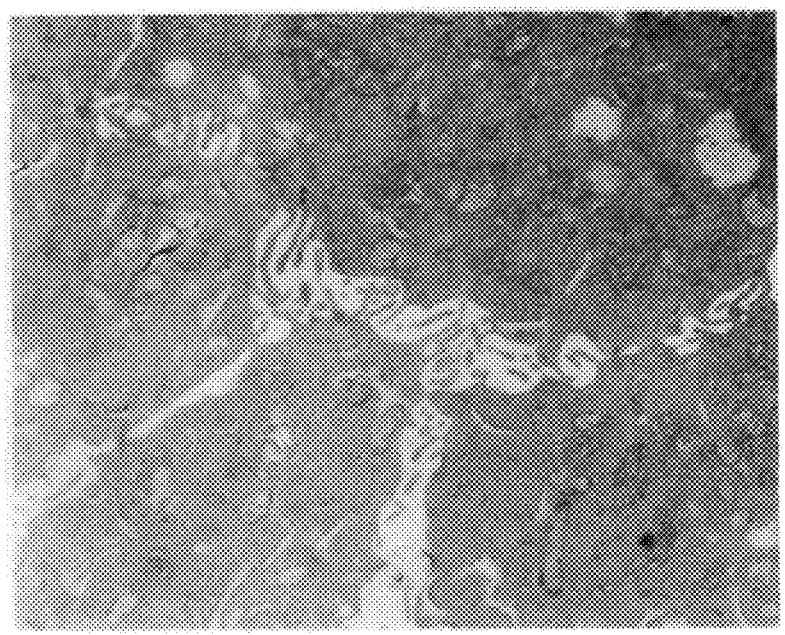
FIG. 5 illustrates upper panel—Ultrastructural appearance of cells composing the cystic structures in solid matrix. Note the microvilli and loss of endosecretory granules. The cells have the appearance of primitive duct-like cells. Lower panel—ultrastructural appearance of cystic structures removed from the solid matrix and placed in suspension culture. Note the decrease in microvilli and the reappearance of endosecretory granules.
Figure 5B:
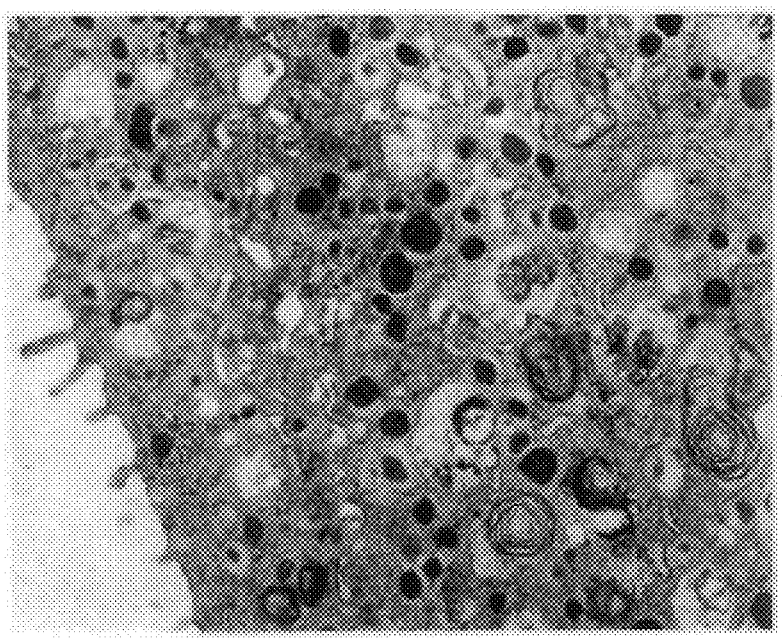
Figure 7:
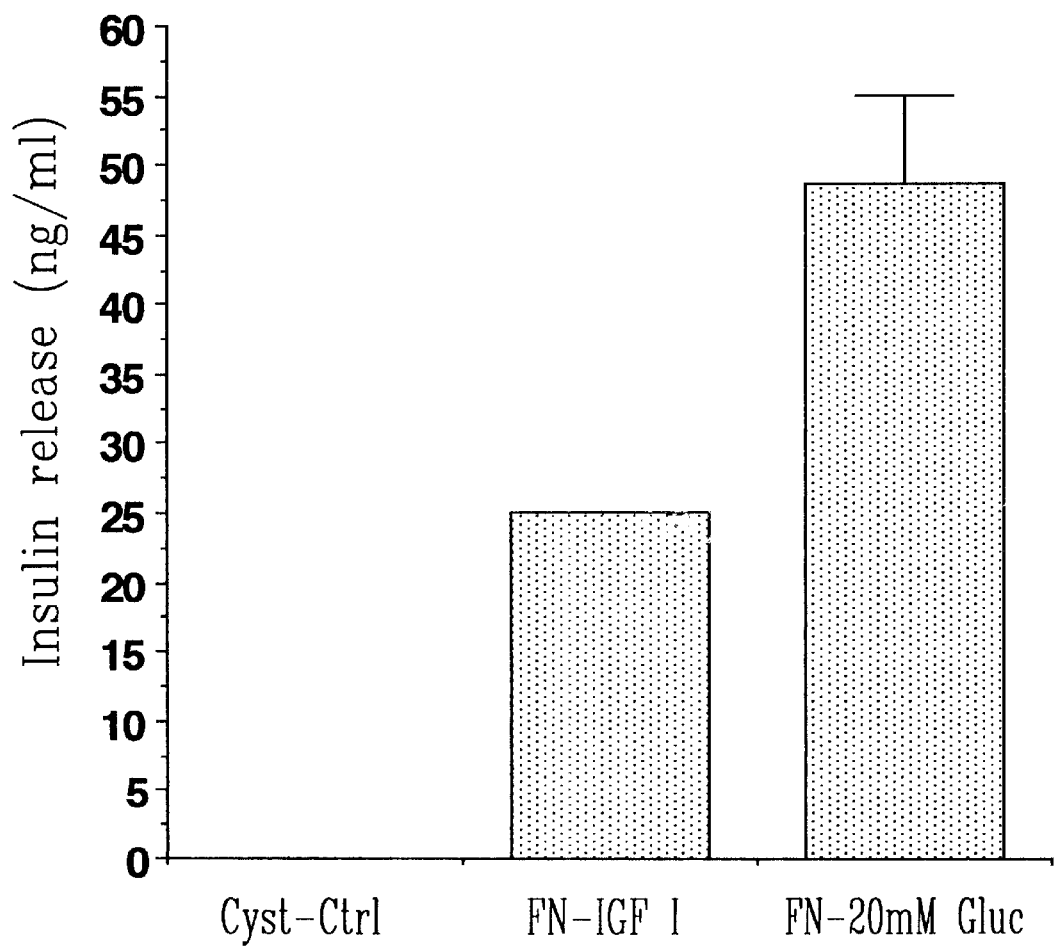
FIG. 7 illustrates insulin release into the culture medium by the structures seen in the lower panel of FIG. 6. Note that there is no demonstrable insulin secreted from the tissue when in the cystic state (far left column). FN-fibronectin; IGF-1-insulin-like growth factor-1; Gluc-glucose.

In vivo cell transformation leading to β-cell neogenesis and new islet formation can be understood in the context of established concepts of developmental biology.

Transdifferentiation is a change from one differentiated phenotype to another, involving morphological and functional phenotypic markers (Okada T S., *Develop. Growth and Differ.* 1986;28:213–321). The best-studied example of this process is the change of amphibian iridial pigment cells to lens fibers, which proceeds through a sequence of cellular dedifferentiation, proliferation and finally redifferentiation (Okada T S, *Cell Diff.* 1983;13:177–183; Okada T S, Kondoh H, *Curr. Top Dev. Biol.,* 1986;20:1–433; Yamada T, *Monogr. Dev. Biol.,* 1977;13:1–124). Direct transdifferentiation without cell division has also been reported, although it is much less common (Beresford W A, *Cell Differ. Dev.,* 1990;29:81–93). While transdifferentiation has been thought to be essentially irreversible, i.e. the transdifferentiated cell does not revert back into the cell type from which it arose, this has recently been reported not to be the case (Danto S I et al., *Am. J. Respir. Cell Mol. Biol.,* 1995;12:497–502). Nonetheless, demonstration of transdifferentiation depends on defining in detail the phenotype of the original cells, and on proving that the new cell type is in fact descended from cells that were defined (Okada T S, *Develop. Growth and Differ.* 1986;28:213–321).

In many instances, transdifferentiation involves a sequence of steps. Early in the process, intermediate cells appear that express neither the phenotype of the original nor the subsequent differentiated cell types, and therefore they have been termed dedifferentiated. The whole process is accompanied by DNA replication and cell proliferation. Dedifferentiated cells are assumed a priori to be capable of forming either the original or a new cell type, and thus are multipotential (Itoh Y, Eguchi G, *Cell Differ.,* 1986;18:173–182; Itoh Y, Eguchi G, *Develop. Biology,* 1986;115:353–362; Okada T S, *Develop. Growth and Differ,* 1986;28:213–321).

Stability of the cellular phenotype in adult organisms is probably related to the extracellular milieu, as well as cytoplasmic and nuclear components that interact to control gene expression. The conversion of cell phenotype is likely to be accomplished by selective enhancement of gene expression, which controls the terminal developmental commitment of cells.

The pancreas is composed of several types of endocrine and exocrine cells, each responding to a variety of trophic influences. The ability of these cells to undergo a change in phenotype has been extensively investigated because of the implications for the understanding of pancreatic diseases such as cancer and diabetes mellitus. Transdifferentiation of pancreatic cells was first noted nearly a decade ago. Hepatocyte-like cells, which are normally not present in the pancreas, were observed following the administration of carcinogen (Rao M S et al., *Am. J. Pathol.,* 1983;110:89–94; Scarpelli D G, Rao M S, *Proc. Nat. Acad. Sci. USA* 1981;78:2577–2581) to hamsters and the feeding of copper-depleted diets to rats (Rao M S, et al., *Cell Differ.,* 1986;18:109–117). Recently, transdifferentiation of isolated acinar cells into duct-like cells has been observed by several groups (Arias A E, Bendayan M, *Lab Invest.,* 1993;69:518–530; Hall P A, Lemoine N R, *J. Pathol.,* 1992;166:97–103; Tsao M S, Duguid W P, *Exp. Cell Res.,* 1987;168:365–375). In view of these observations it is probably germane that during embryonic development, the hepatic and pancreatic anlagen are derived from a common endodermal.

An alternative to transdifferentiation, is the possibility that new islet cells arise from stem cells that persist post-natally in adult tissue.

There are two general categories of stem cells (Young H E et al. *PSEBM* 1999; 221:63–71; Young H E et al. *Wound Rep Regen* 1998; 6:65–75). Progenitors are (a) lineage committed (i.e. they will form only tissues within their respective committed lineages(s)); (b) they prefer to remain quiescent and therefore need to be actively stimulated or challenged to do anything; (c) their life-span is approx. 50–70 cell divisions before programmed cell death intervenes; (d) they are unresponsive to inductive agents outside their lineage; and (e) they are responsive to progression agents (e.g. insulin, IGF-1 or IGF-2) which are needed to promote phenotypic expression into lineage restricted phenotypes only. Pluripotents, on the other hand, are lineage uncommitted, derived from the inner cell mass of the blastocyst.

Within these two broad categories, there are four types of cells—(1) the totipotent stem cell; (2) the pluripotent stem cell; (3) the multipotent stem cell, and (4) the unipotent stem cell. Multipotent cells (committed to two or more cell lineage, e.g. chondro-osteogenic, adipo-fibrogenic) and unipotent cells (committed to a single tissue lineage, e.g. myogenic, adipogenic, osteogenic), are considered to be progenitor cells. To date, progenitor cells have been identified from six species thus far, and also from fetal to geriatric aged individuals. It is quite possible, therefore, that islet cell differentiation post-natally may occur as a result of the stimulation of a unipotent or multipotent progenitor cell as opposed to transdifferentiation.

One example of such a mechanism can be observed in the liver. Hepatic oval cells are a small sub-population of cells found in the liver when hepatocyte proliferation is inhibited and followed by some type of hepatic injury. They are believed to be bipotential, able to differentiate into into hepatocytes or bile duct epithelium. They express the same markers as hematopoietic stem cells (HSC), and evidence has been obtained that these cells can be derived from a bone marrow source (Petersen B E, et al. *Science* 1999;284:1168–1170). In this context, it is quite possible that the hepatocyte-like cells identified in the pancreas, to which we referred above (Rao M S et al., *Am. J. Pathol.,* 1983;110:89–94; Scarpelli D G, Rao M S, *Proc. Nat. Acad. Sci. USA* 1981;78:2577–2581; Rao M S, et al., *Cell Differ.,* 1986;18:109–117), may have in fact been derived from the equivalent of oval cells in the pancreas.

Factors which control the growth and functional maturation of the human endocrine pancreas during the fetal and post-natal periods are still poorly understood, although the presence of specific factors in the pancreas has been hypothesized (Pictet R L et al. In: Extracellular Matrix Influences on Gene Expression. Slavkin H C, Greulich R C (eds). Academic Press, New York, 1975, pp.10).

Some information is available on exocrine growth factors. Mesenchymal Factor (MF), has been extracted from particulate fractions of homogenates of midgestational rat or chick embryos. MF affects cell development by interacting at the cell surface of precursor cells (Rutter W J. The development of the endocrine and exocrine pancreas. In: The Pancreas. Fitzgerald P J, Morson A B (eds). Williams and Wilkins, London, 1980, pp.30) and thereby influences the kind of cells that appear during pancreatic development (Githens S. Differentiation and development of the exocrine pancreas in animals. In: Go V L W, et al. (eds) The Exocrine Pancreas: Biology, Pathobiology and Diseases. Raven Press, New York, 1986, pp.21). MF is comprised of at least 2 fundamental components, a heat stable component whose action can be duplicated by cyclic AMP analogs, and another high molecular weight protein component (Rutter W J, In: The Pancreas. Fitzgerald P J, Morson A B (eds). Williams and Wilkins, London, 1980, pp.30). In the presence of MF, cells divide actively and differentiate largely into non-endocrine cells.

Other factors have also been implicated in endocrine maturation. Soluble peptide growth factors (GF) are one group of trophic substances that regulate both cell proliferation and differentiation. These growth factors are multifunctional and may trigger a broad range of cellular responses (Sporn & Roberts, *Nature,* 332:217–19, 1987). Their actions can be divided into 2 general categories—effects on cell proliferation, which comprises initiation of cell growth, cell division and cell differentiation; and effects on cell function. They differ from the polypeptide hormones in that they act in an autocrine and/or paracrine manner (Goustin A S, Leof E B, et al. *Cancer Res.,* 46:1015–1029, 1986; Underwood L E, et al., *Clinics in Endocrinol. & Metabol.,* 15:59–77,1986). Specifics of their role in the individual processes that comprise growth need to be resolved.

One family of growth factors are the somatomedins. Insulin-like growth factor-I (IGF-I), is synthesized and released in tissue culture by the $\beta$-cells of fetal and neonatal rat islets (Hill D J, et al., *Diabetes,* 36:465–471, 1987; Rabinovitch A, et al., *Diabetes,* 31:160–164,1982; Romanus J A et al., *Diabetes* 34:696–792, 1985). IGF-II has been identified in human fetal pancreas (Bryson J M et al., *J. Endocrinol.,* 121:367–373,1989). Both these factors enhance neonatal $\beta$-cell replication in vitro when added to the culture medium (Hill D J, et al., *Diabetes,* 36:465–471, 1987; Rabinovitch A, et al., *Diabetes,* 31:160–164, 1982). Therefore the IGF's may be important mediators of cell replication in fetal and neonatal rat islets but may not do so in post-natal development (Billestrup N, Martin J M, *Endocrinol.,* 116:1175–81,1985; Rabinovitch A, et al., *Diabetes,* 32:307–12, 1983; Swenne I, Hill D J, *Diabetologia* 32:191–197, 1989; Swenne I, *Endocrinology,* 122:214–218, 1988; Whittaker P G, et al, *Diabetologia,* 18:323–328, 1980). Furthermore, Platelet-derived growth factor (PDGF) also stimulates fetal islet cell replication and its effect does not require increased production of IGF-I (Swenne I, *Endocrinology,* 122:214–218, 1988). Moreover, the effect of growth hormone on the replication of rat fetal β-cells appears to be largely independent of IGF -I (Romanus J A et al., *Diabetes* 34:696–792, 1985; Swenne I, Hill D J, *Diabetologia* 32:191–197, 1989). In the adult pancreas, IGF-I mRNA is localized to the D-cell. But IGF-I is also found on cell membranes of β- and A-cells, and in scattered duct cells, but not in acinar or vascular endothelial cells (Hansson H-A et al., *Acta Physiol. Scand.* 132:569–576, 1988; Hansson H-A et al., *Cell Tissue Res.,* 255:467–474, 1989). This is in contradistinction to one report (Smith F et al, *Diabetes,* 39 (suppl 1):66A, 1990), wherein IGF-I expression was identified in ductular and vascular endothelial cells, and appeared in regenerating endocrine cells after partial pancreatectomy. It has not been shown that IGF's will stimulate growth of adult duct cells or islets. Nor do the IGF's stimulate growth of the exocrine pancreas (Mossner J et al., *Gut* 28:51–55, 1987). It is apparent therefore, that the role of IGF-I, especially in the adult pancreas, is far from certain.

Fibroblast growth factor (FGF) has been found to initiate transdifferentiation of the retinal pigment epithelium to neural retinal tissues in chick embryo in vivo and in vitro (Hyuga M et al., *Int. J. Dev. Biol.* 1993;37:319–326; Park C M et al., *Dev. Biol.* 1991;148:322–333; Pittack C et al., *Development* 1991;113:577–588). Transforming growth factor-beta (TGF-β) has been demonstrated to induce transdifferentiation of mouse mammary epithelial cells to fibroblast cells [20]. Similarly, epithelial growth factor (EGF) and cholera toxin were used to enhance duct epithelial cyst formation from among pancreatic acinar cell fragments (Yuan S et al., *In vitro Cell Dev. Biol.,* 1995;31:77–80).

The search for the factors mediating cell differentiation and survival must include both the cell and its microenvironment (Bissell M J et al., *J. Theor. Biol.,* 1982; 99:31), as a cell's behavior is controlled by other cells as well as by the extracellular matrix (ECM) (Stoker A W et al. *Curr. Opin. Cell. Biol.,* 1990;2:864). ECM is a dynamic complex of molecules serving as a scaffold for parenchymal and non-parenchymal cells. Its importance in pancreatic development is highlighted by the role of fetal mesenchyme in epithelial cell cytodifferentiation (Bencosme S A,*Am. J. Pathol.* 1955; 31: 1149; Gepts W, de Mey J. *Diabetes* 1978; 27(suppl. 1): 251; Gepts W, Lacompte P M. *Am. J. Med.,* 1981; 70: 105; Gepts W. *Diabetes* 1965; 14: 619; Githens S. In: Go V L W, et al. (eds) The Exocrine Pancreas: Biology, Pathobiology and Disease. (New York: Raven Press, 1986) p. 21). ECM is found in two forms—interstitial matrix and basement membrane (BM). BM is a macromolecular complex of different glycoproteins, collagens, and proteoglycans. In the pancreas, the BM contains laminin, fibronectin, collagen types IV and V, as well as heparan sulphate proteoglycans (Ingber D. In: Go V L W, et al (eds) The Pancreas: Biology, Pathobiology and Disease (New York: Raven Press, 1993) p. 369). The specific role of these molecules in the pancreas has yet to be determined.

ECM has profound effects on differentiation. Mature epithelia that normally never express mesenchymal genes, can be induced to do so by suspension in collagen gels in vitro (Hay E D. *Curr. Opin. in Cell. Biol.* 1993; 5:1029). For example, mammary epithelial cells flatten and lose their differentiated phenotype when attached to plastic dishes or adherent collagen gels (Emerman J T, Pitelka D R. *In vitro* 1977; 13:316). The same cells round, polarize, secrete milk proteins, and accumulate a continuous BM when the gel is allowed to contract (Emerman J T, Pitelka D R. *In vitro,* 1977; 13:316). Thus different degrees of retention or re-formation of BM are crucial for cell survival and the maintenance of the normal epithelial phenotype (Hay E D. *Curr. Opin. in Cell. Biol.* 1993; 5:1029).

During times of tissue proliferation, and in the presence of the appropriate growth factors, cells are transiently released from ECM-determined survival constraints. It is now becoming clear that there are two components of the cellular response to ECM interactions—one physical, involving shape changes and cytoskeletal organization; the other biochemical, involving integrin clustering and increased protein tyrosine phosphorylation (Ingber D E. *Proc. Natl. Acad. Sci. USA,* 1990;87:3579; Roskelley C D et al., *Proc. Natl. Acad. Sci. USA,* 1994;91:12378)

In addition to its known regulatory role in cellular growth and differentiation, ECM has more recently been recognized as a regulator of cell survival (Bates R C, Lincz L F, Burns G F, *Cancer and Metastasis Rev.,* 1995;14:191). Disruption of the cell-matrix relationship leads to apoptosis (Frisch S M, Francis H. *J. Cell. Biol.,* 1994;124:619; Schwartz S M, Bennett M R, *Am. J. Path.,* 1995;147:229), a morphological series of events (Kerr J F K et al., *Br. J. Cancer,* 1972;26:239), indicating a process of active cellular self destruction.

In accordance with one embodiment of the present invention, the platform technology is based on a combination of the foregoing observations, incorporating the following components that are necessary and sufficient for the preparation of dedifferentiated intermediate cells from adult pancreatic islets of Langerhans:

1. a solid matrix permitting "three dimensional" culture;
2. the presence of matrix proteins including but not limited to collagen type I and laminin; and
3. the growth factor EGF and promoters of cAMP, including but not limited to cholera toxin and forskolin.

The preferred feeding medium is DMEM/F12 with 10% fetal calf serum. In addition, the starting tissue must be freshly isolated and cultured without absolute purification.

The use of a matrix protein-containing solid gel is an important part of the culture system, because extracellular matrix may promote the process of transdifferentiation. This point is highlighted by isolated pancreatic acinar cells, which transdifferentiate to duct-like structures when entrapped in Matrigel basement membrane (Arias A E, Bendayan M, *Lab Invest.,* 1993;69:518–530), or by retinal pigmented epithelial cells, which transdifferentiate into neurons when plated on laminin-containing substrates (Reh T A et al., *Nature* 1987;330:68–71). Most recently, Gittes et al. demonstrated, using 11-day embryonic mouse pancreas, that the default path for growth of embryonic pancreatic epithelium is to form islets (Gittes G K et al., *Development* 1996; 122:439–447). In the presence of basement membrane constituents, however, the pancreatic anlage epithelium appears to programmed to form ducts. This finding again emphasizes the interrelationship between ducts and islets and highlights the important role of the extracellular matrix.

This completes stage 1 (the production of dedifferentiated intermediate cells) of the process. During the initial 96 h of culture, islets undergo a cystic transformation associated with (Arias A E, Bendayan M, *Lab. Invest.*, 1993;69:518–530) a progressive loss of insulin gene expression, (2) a loss of immunoreactivity for insulin protein, and (3) the appearance of CKA 19, a marker for ductal cells. After transformation is complete, the cells have the ultrastructural appearance of primitive duct-like cells. Cyst enlargement after the initial 96 h is associated, at least in part, with a tremendous increase in cell replication. These findings are consistent with the transdifferentiation of an islet cell to a ductal cell (Yuan et al., *Differentiation*, 1996; 61:67–75).

Stage 2—the generation of functioning β-cells, requires a complete change of the culture conditions. The cells are moved from the digested matrix and resuspended in a basal liquid medium such as CMRL 1066 supplemented with 10% fetal calf serum, with the addition of soluble matrix proteins and growth factors that include, but are not limited to, fibronectin (10–20 ng/ml), IGF-1 (100 ng/ml), IGF-2 (100 ng), insulin (10–100 μg/ml), NGF (10–100 ng/ml). In addition, the glucose concentration must be increased to above 11 mM. Additional culture additives may include specific inhibitors of known intracellular signaling pathways of apoptosis, including, but not limited to a specific inhibitor of p38.

Evidence for the return to an islet cell phenotype includes: (1) the re-appearance of solid spherical structures; (2) loss of CK-19 expression; (3) the demonstration of endosecretory granules on electron microscopy; (4) the re-appearance of pro-insulin mRNA on in situ hybridization; (5) the return of a basal release of insulin into the culture medium.

The present invention will be more readily understood by referring to the following examples which are given to illustrate the invention rather than to limit its scope.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An in vitro method for islet cell expansion, which comprises the steps of:
   a) inducing cystic formation in cells in or associated with post-natal islets of Langerhans to obtain a duct-like structure;
   b) expanding cells of said duct-like structure; and
   c) inducing islet cell differentiation of said expanded cells of said duct-like structure to become insulin-producing cells;

wherein step a) and step b) are concurrently effected using a solid matrix, basement membrane constituents, basal feeding medium and appropriate growth factors to permit the development, maintenance and expansion of a duct-like structure cell population with at least bipotentiality;

wherein step c) is effected by removing cells from said matrix and resuspended in a basal liquid medium containing soluble matrix proteins and growth factors selected from the group consisting of fibronectin, IGF-1, IGF-2, insulin, and NGF.

2. The method of claim 1, wherein said basal liquid medium is CMRL 1066 supplemented with 10% fetal calf serum.

3. The method of claim 1, wherein said basal liquid medium further comprises glucose concentration of at least 11 mM.

4. The method of claim 3, wherein said basal liquid medium further comprises inhibitors of known intracellular signaling pathways of apoptosis and/or specific inhibitor of p38.

* * * * *